United States Patent [19]
Brown

[11] Patent Number: 6,059,763
[45] Date of Patent: May 9, 2000

[54] COMBINATION TAMPON AND MENSTRUAL PAD

[76] Inventor: Norma Brown, 2721 Kings Hwy., Apt. 4M, Brooklyn, N.Y. 11229

[21] Appl. No.: 09/055,157
[22] Filed: Apr. 4, 1998
[51] Int. Cl.[7] ...................................................... A61F 13/15
[52] U.S. Cl. .......................... 604/385.1; 604/11; 604/386
[58] Field of Search ................................... 604/385.1, 11, 604/386

[56] References Cited

U.S. PATENT DOCUMENTS 5,057,096 10/1991 Faglione .
5,824,004 10/1998 Osbom, III et al. .

Primary Examiner—John G. Weiss
Assistant Examiner—Kelvin Hart
Attorney, Agent, or Firm—Michael I. Kroll

[57] ABSTRACT

An absorbent pad for absorbing bodily fluid secreted from a user. The absorbent pad includes a base pad having first and second length sides and first and second wings. The first and second wings each extending along a respective one of the first and second length sides. The absorbent pad also includes a tampon extending substantially perpendicular to the base pad at a central portion thereof, wherein, in use, the tampon is positioned within a body opening of the user and the base pad is positioned outside the body opening and between legs of the user to absorb body fluids secreted from the body opening. The tampon may be removably connected to the base pad and a gluteal pad may be connected to extend from an end side of the base pad. The gluteal pad includes a fold positioned within the user's buttocks during use. Lateral borders may be positioned between the sides of the base pad and the wings extending therefrom for providing added absorption of secreted bodily fluids. An adhesive strip may also be positioned on an underside of the base pad for securing the absorbent pad to the undergarment of the user.

13 Claims, 4 Drawing Sheets

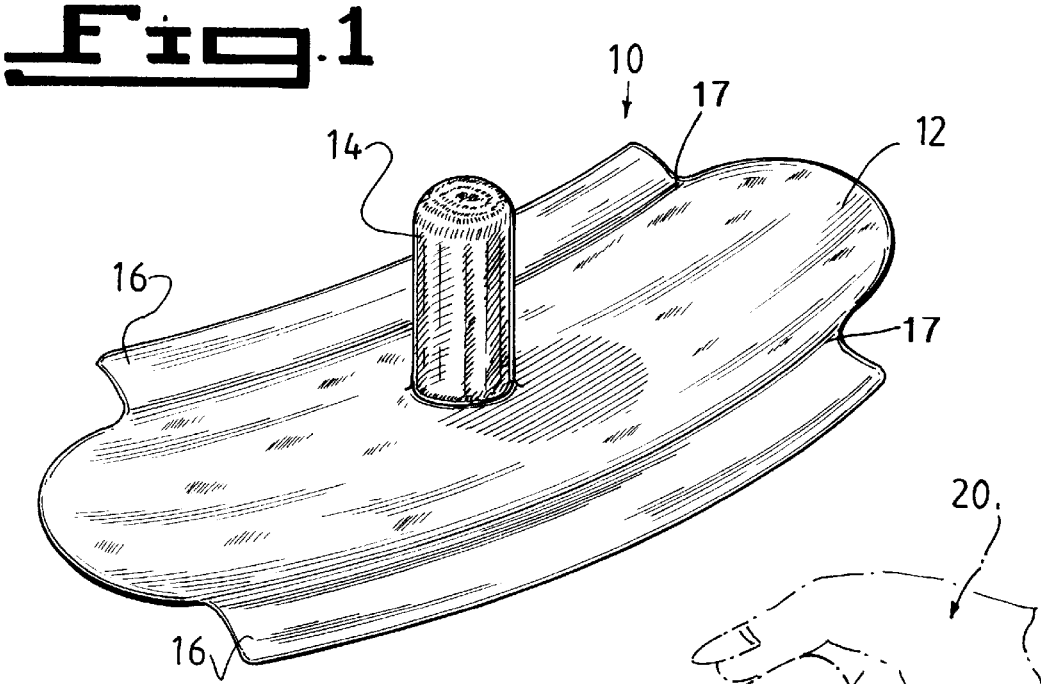
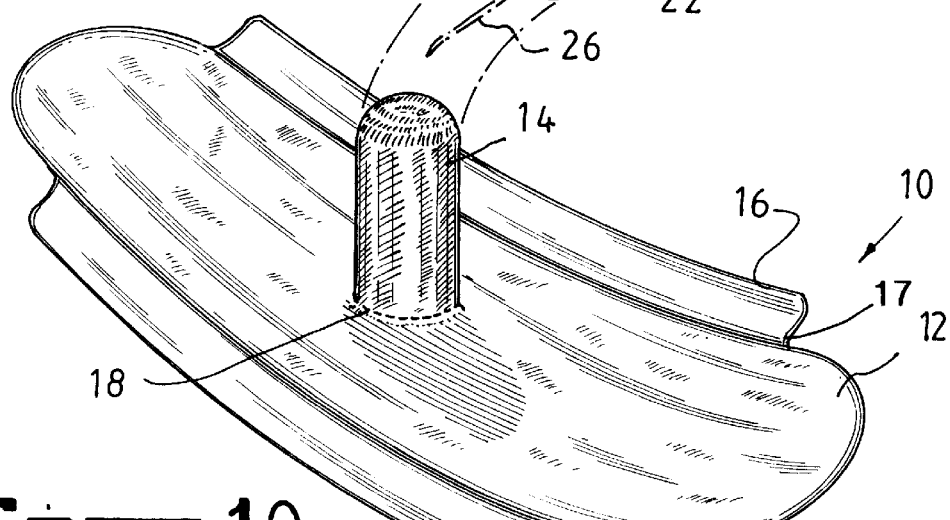

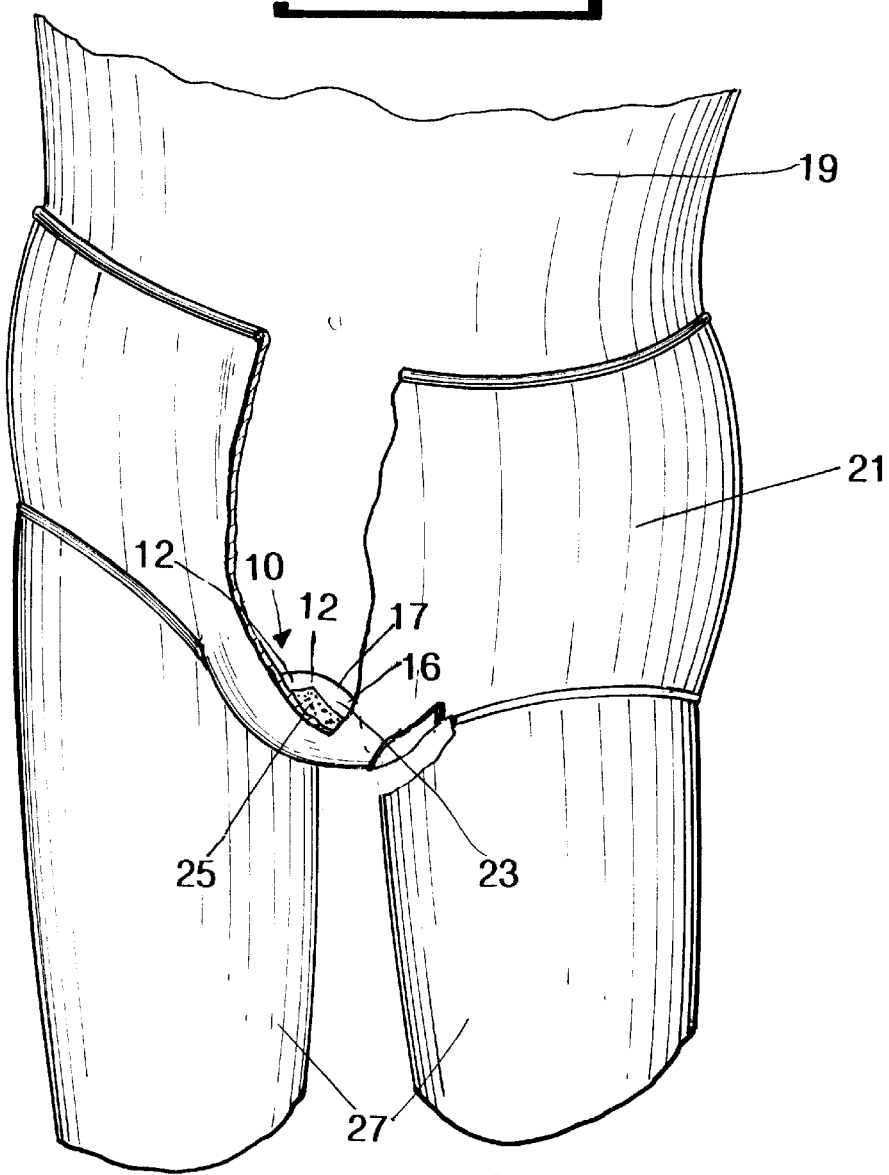
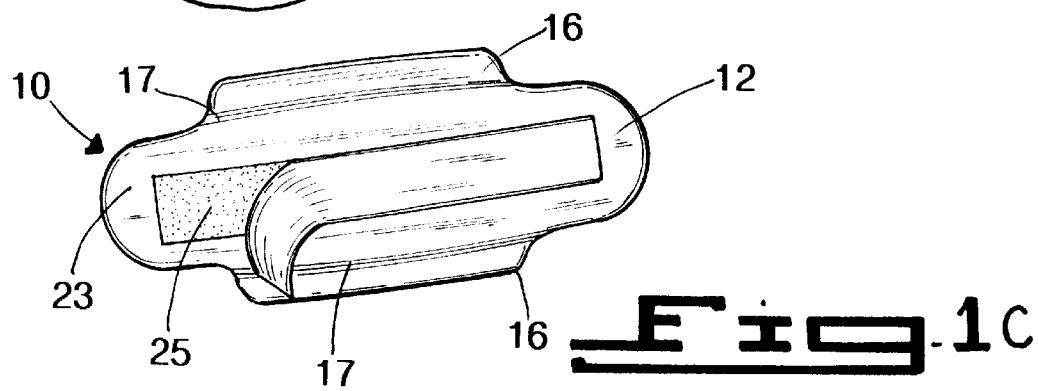

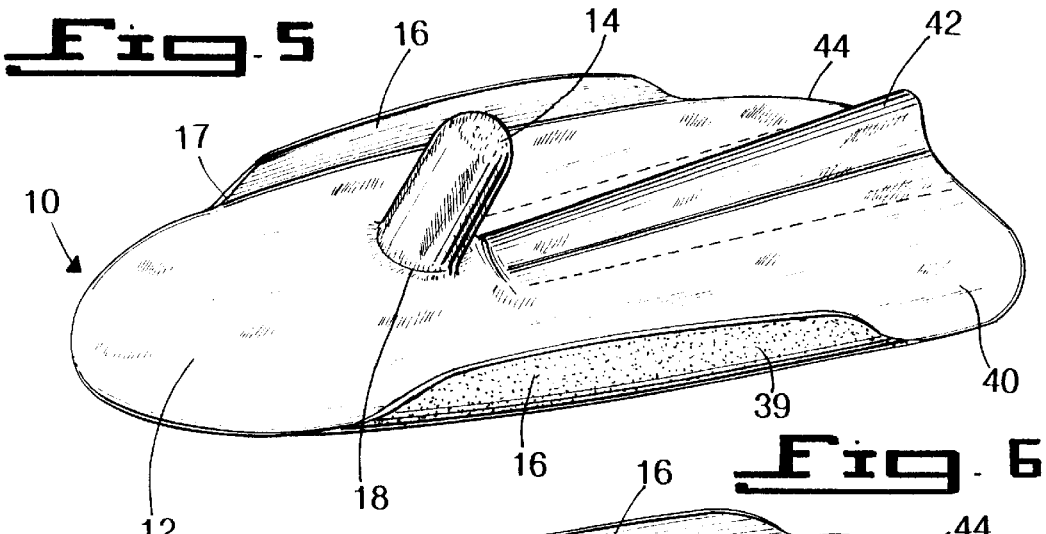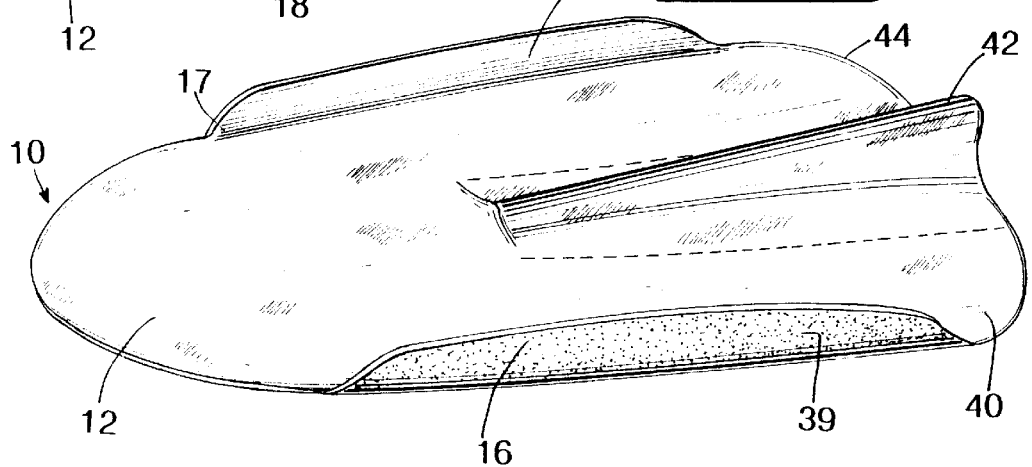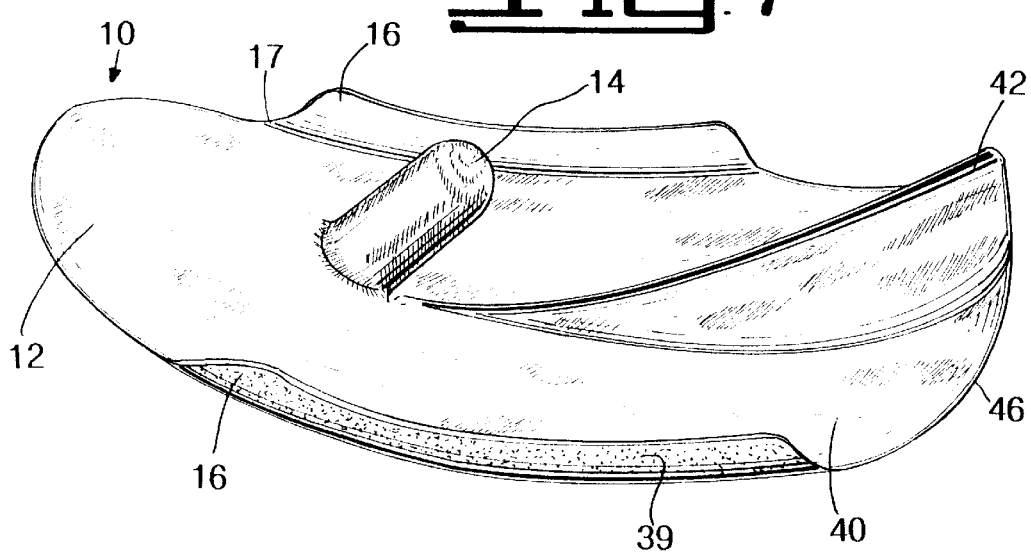

COMBINATION TAMPON AND MENSTRUAL PAD

BACKGROUND OF THE INVENTION

1. Field of the Invention

The present invention relates generally to tampons and menstrual pads and, more specifically, to a combination tampon and menstrual pad which provides the benefits of both pads while increasing the amount of absorption of secreted bodily fluids and reducing the effects of spillage or the occurrence of accidents accompanying movement of a woman into a horizontal position caused by secreted bodily fluids.

2. Description of the Prior Art

Numerous types of tampons and menstrual pads have been provided in the prior art. For example, U.S. Pat. Nos. 4,351,339; 5,403,300; 5,554,108 and 5,688,257 all are illustrative of such prior art. While these units may be suitable for the particular purpose to which they address, they would not be as suitable for the purposes of the present invention as heretofore described.

U.S. Pat. No. 4,351,339

Inventor: Vincent R. Sneider

Issued: Sep. 28, 1982

A tampon assembly for use with and in body openings, said tampon having a close helically-wound absorbent member with the portions substantially parallel and contiguous to provide an outer support surface for a permeable cover that is pleated. The pleated cover has the folds overlaid so that in an inserting condition the pleats are disposed to retain their overlaid positions during insertion. An inserting stick or rod is conventionally used for insertion. A withdrawal string is attached to the absorbent member at that end that faces the body opening. The cover at its withdrawal end captures the withdrawal string so that at the time of withdrawal the string is grasped and the cover and spiral wound absorbent member is manipulated from the opening causing at least a partial collapse of the absorbent member into a smaller diameter and with the string also withdrawing the pleated cover with the folds in said cover being unfolded to bring the cover into an unfolded condition and removal of the tampon assembly from the body opening is easily made with a reduction in diameter of the tampon.

U.S. Pat. No. 5,403,300

Inventor: George Howarth

Issued: Apr. 4, 1995

A tampon for hygienic use comprising a generally cylindrical absorbent core having a liquid pervious cover layer on the outer surface thereof wherein the cover layer is a polymer net comprising two intersecting sets of parallel ribs and wherein each set of ribs are aligned obliquely with respect to both the main axis of the tampon and to each other. A strip of net may be bonded to one end of a strip of absorbent material and the composite spirally wound such that the net forms the outer layer. The free end of the net may overlap an underlying layer of net and be bonded thereto by heat sealing.

U.S. Patent Number 5,554,108

Inventor: John H. D. Browning et al.

Issued: Sep. 10, 1996

The present invention relates to a sanitary tampon comprising a compact applicator and a tampon of compressed absorbent material stored within the applicator, the applicator having an inner tube and an outer tube slidably disposed over the inner tube. The outer tube has a distal discharge end for insertion into the body of the user. The tampon is solid and substantially cylindrical in shape and is constructed such that at least a part of the body of the tampon adjacent the proximal end sits at an angle to the longitudinal axis of the applicator so that when the inner tube is withdrawn past the proximal end of the tampon to prime the applicator for use, the proximal end of the tampon will urge itself against the inner surface of the outer tube and when the inner tube is pushed back into the outer tube to expel the tampon, the tampon is hindered from re-entering the distal end of the inner tube.

U.S. Pat. No. 5,688,257

Inventor: Clas Olsen

Issued: Nov. 18, 1997

A tampon includes an absorbent body which is embraced by a fluid-permeable casing of the thermoplastic non-woven material. A withdrawal string attached to the absorbent body exits centrally from one end surface of the tampon. The casing material is heat-sealed at least at the central part of the end surface, by pressing a mandrel against the end of the tampon, so as to coalesce the thermoplastic material to an essentially fluid-impervious film. This improves the protection of the tampon against leakage and also increases the stability of the tampon.

SUMMARY OF THE PRESENT INVENTION

The present invention relates generally to tampons and menstrual pads and, more specifically, to a combination tampon and menstrual pad which provides the benefits of both pads while increasing the amount of absorption of secreted bodily fluids and reducing the effects of spillage or the occurrence of accidents accompanying movement of a woman into a horizontal position caused by secreted bodily fluids.

A primary object of the present invention is to provide a combination tampon and menstrual pad that will overcome the shortcomings of prior art devices.

Another object of the present invention is to provide a combination tampon and menstrual pad wherein a tampon is connected to extend substantially perpendicular to a horizontally extending base pad, the combination tampon and menstrual pad being positioned in the groin area of the user and beneath the user's undergarment whereby the tampon is positioned to extend into a body opening.

An additional object of the present invention is to provide a combination tampon and menstrual pad including a perforated connection between the tampon and horizontally extending base pad allowing the tampon to be removed and used separately from the base pad.

A further object of the present invention is to provide a combination tampon and menstrual pad including wings extending from the horizontally extending base pad for overlapping the sides of the user's undergarment providing additional support and undergarment protection.

A yet further object of the present invention is to provide a combination tampon and menstrual pad including a gluteal pad extending from an end of the horizontally extending base pad for providing additional absorption of backward spillage occurring when a woman lies in a horizontal position.

Another object of the present invention is to provide a combination tampon and menstrual pad that is simple and easy to use.

A still further object of the present invention is to provide a combination tampon and menstrual pad that is economical in cost to manufacture.

Additional objects of the present invention will appear as the description proceeds.

A combination tampon and menstrual pad for absorbing bodily fluids secreted through a body opening of a user is described by the present invention. The combination tampon and menstrual pad includes a base pad having first and second length sides and first and second wings. The first and second wings each extending along a respective one of the first and second length sides. The combination tampon and menstrual pad also includes a tampon extending substantially perpendicular to the base pad at a substantially central portion thereof, wherein, in use, the tampon is positioned to extend into a body opening of the user and the base pad is positioned outside the body opening and between the legs of the user to absorb body fluids secreted from the body opening. The tampon may be removably connected to the base pad whereby the tampon can be removed and used independently of the base pad. Furthermore, a gluteal pad may be connected to extend from an end side of the base pad. The gluteal pad includes a fold for positioning within the user's buttocks to absorb any body fluids which may spill from the area in which secretion occurred due to movement of the user. Lateral borders may be positioned between the sides of the base pad and the wings extending therefrom for providing added absorption of secreted bodily fluids. An adhesive strip may also be positioned on an underside of the base pad for securing the absorbent pad to the undergarment of the user.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 1 is a perspective view of the combination tampon and menstrual pad of the present invention;

FIG. 1a is a perspective view of the combination tampon and menstrual pad of the present invention including a perforated connection between the tampon and base pad whereby the tampon is detachable from the base pad as shown in dot-dashed lines;

FIG. 1b is a partial cross-sectional side perspective view with parts cut away of the combination tampon and menstrual pad of the present invention as worn by a user;

FIG. 1c is a bottom plan view of the combination tampon and menstrual pad of the present invention;

FIG. 5 is a top perspective view of the combination tampon and menstrual pad of the present invention including a gluteal pad extending from an end of the base pad for positioning between a user's buttocks;

FIG. 6 is a bottom perspective view of the combination tampon and menstrual pad of the present invention including the gluteal pad and without the tampon extending from the base pad; and FIG. 7 is a top perspective view of the combination tampon and menstrual pad of the present invention including a gluteal pad.

DESCRIPTION OF THE REFERENCED NUMERALS

Figure 2:
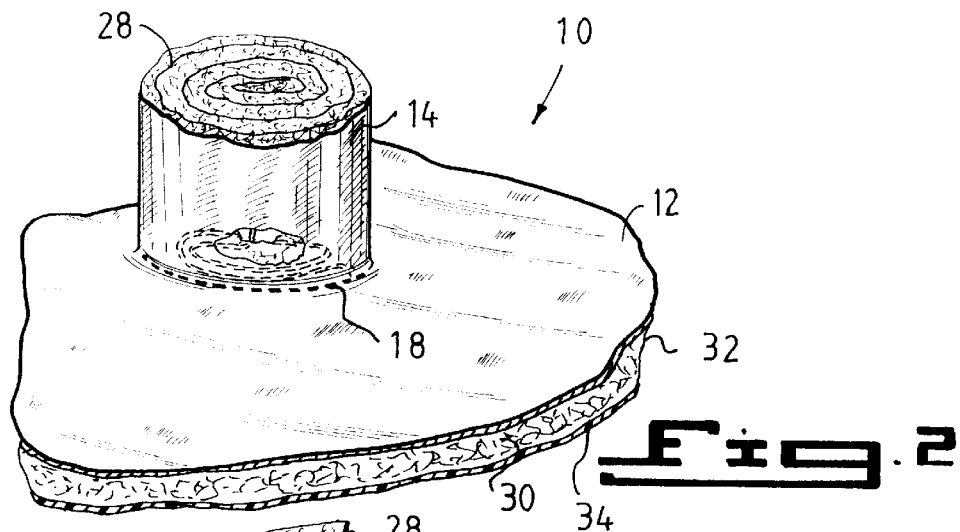
FIG. 2 is an exploded perspective cross-sectional view of the tampon portion of the combination tampon and menstrual pad of the present invention.

Turning now descriptively to the drawings, in which similar reference characters denote similar elements throughout the several views, the Figures illustrate the combination tampon and menstrual pad of the present invention. With regard to the reference numerals used, the following numbering is used throughout the various drawing figures.

10 combination tampon and menstrual pad of the present invention
12 horizontally extending base pad
14 tampon connected to extend vertically from base pad
16 wings extending from pad
17 lateral borders
18 perforated connection between tampon and base pad
19 user of the combination tampon and menstrual pad
20 user's hand
21 undergarment of user
22 removed tampon portion of combination tampon and menstrual pad
23 base side of horizontally extending base pad
24 base of tampon
25 adhesive strip on base side of horizontally extending base pad
26 string of tampon material
27 legs of user
28 rolled compressed material forming tampon
29 cover strip
30 absorbent material forming base pad
32 upper layer of base pad
34 lower layer of base pad
36 seal between tampon and base pad
38 perforation between adjacent seals between tampon and base pad
39 adhesive material on back of wings
40 gluteal pad
42 fold in gluteal pad for positioning within buttocks of user
44 tapered edge of gluteal pad

DETAILED DESCRIPTION OF THE PREFERRED EMBODIMENT

Turning now descriptively to the drawings, in which similar reference characters denote similar elements throughout the several views, FIGS. 1–7 illustrate the combination tampon and menstrual pad of the present invention. The combination tampon and menstrual pad of the present invention is indicated generally by the numeral 10.

As can be seen from FIG. 1, the combination tampon and menstrual pad 10 includes a horizontally extending base pad 12 and a tampon 14 connected to the horizontally extending base pad 12 at a central portion thereof. The tampon 14 is connected to extend vertically from the horizontally extending base pad 12 at an angle substantially perpendicular thereto. On either side of the horizontally extending base pad 12 and extending along the length thereof are wings 16. Positioned or-either side of the base pad 12 and acting to connect each of the wings 16 to the horizontally extending base pad 12 is a lateral border 17.

As is illustrated in FIG. 1b, the horizontally extending base pad 12 is positioned in the groin area of a user 19 and beneath the undergarment 21. The tampon 14 is positioned to extend vertically from the horizontally extending base pad 12 and into a body opening of the user 19. The wings 16 extend from the lateral borders 17 at the sides of the horizontally extending base pad 12 so as to overlap and wrap around the sides of the undergarment 21. The wings 16 thereby provide added protection for the undergarment 21 from soiling by secreted bodily fluids spliiling over the sides of the base pad 12. The lateral borders 17 provide additional absorption of secreted bodily fluids spilling over the sides of the base pad 12. The wings 16 also add support and stability to both the horizontally extending base pad 12 and the tampon 14 to thereby prevent unintended movement and sliding of the tampon 14 and horizontally extending base pad 12. On an underside 23 of the horizontally extending base pad 12 is an adhesive strip 25. The adhesive strip 25 will secure the base pad 12 to the undergarment 21 and thereby provide additional support against movement of the combination tampon and menstrual pad 10. The underside 23 of the combination tampon and menstrual pad 10 is shown in FIG. 1c which also clearly illustrates the adhesive strip 25. The combination tampon and menstrual pad 10 is thus able to remain in position between the legs 27 of the user 19 and absorb any fluid secreted by and exiting the body of the user 19.

FIG. 1a illustrates the combination tampon and menstrual pad 10 of the present invention including a perforated connection 18 between the tampon 14 and the horizontally extending base pad 12. The perforated connection 18 allows the tampon 14 to be removed from the horizontally extending base pad 12 as illustrated in dot-dashed lines. The tampon 14 may be removed at the discretion of the user to thereby allow separate and independent use of the tampon 14 and horizontally extending base pad 12.

This figure illustrates a user's hand 20 removing the tampon portion 22 of the combination tampon and menstrual pad 10 from the horizontally extending base pad 12 for separate use. The tampon portion 22 is removed by a combination twisting and pulling action. Extending from a base 24 of the tampon portion 22 is a string of tampon material 26 which aids in maintaining the connection between the tampon 14 and horizontally extending base pad 12. The string of tampon material 26 joins the material comprising the tampon 14 and horizontally extending base pad 12, integrally connecting the tampon 14 and horizontally extending base pad 12 together prior to separation of the tampon portion 22 from the horizontally extending base pad 12. The connection between the tampon 22 and horizontally extending base pad 12 can be more clearly seen and will be described further with reference to FIG. 4 hereinafter.

The underside 23 of the combination tampon and menstrual pad 10 is illustrated in FIG. 1c. From this figure, the adhesive strip 25 is shown extending along the length of the base pad 12. The adhesive strip 25 is used to secure the base pad 12 to the undergarment 21 and thereby provide added support and stability against movement and sliding of the combination tampon and menstrual pad 10 within the undergarment 21. Prior to use a cover strip 29 is used to cover the adhesive strip 25 and prevent sticking to any unintended surface.

A partial cross-sectional view of the tampon 14 and horizontally extending base pad 12 can be seen from FIG. 2. This figure is an exploded view illustrating the composition of the tampon 14 and horizontally extending base pad 12. As can be seen from this figure the tampon portion 14 of the combination tampon and menstrual pad 10 is formed from a rolled compressed material 28. This material 28 is an absorbent material able to soak up secretions of bodily fluids coming from the body opening in which it is positioned. The horizontally extending base pad 12 includes a middle layer 30 of absorbent material positioned between and sandwiched by an upper layer 32 and a lower layer 34. The upper and lower layers 32 and 34, respectively, are preferably formed of a liquid permeable material which will retain any liquid passing therethrough therebetween for absorption by the middle layer 30. The rolled compressed material 28 forming the tampon 14 is further detachably connected to the layer 30 of absorbent material forming the horizontally extending base pad 12. This connection improves the absorbency of the tampon 14 as there is now a larger surface area for absorbing fluids secreted from the body opening of the user. The secreted fluids unable to be absorbed by the tampon 14 can be absorbed and held within the absorbent material forming the middle layer 30 of the horizontally extending base pad 12. Furthermore, any secreted fluids absorbed by the tampon 14 can be transported through the tampon 14 for capture and absorption by the horizontally extending base pad 12 thereby providing a larger absorption area in which the secreted fluids can be retained.

Figure 3:
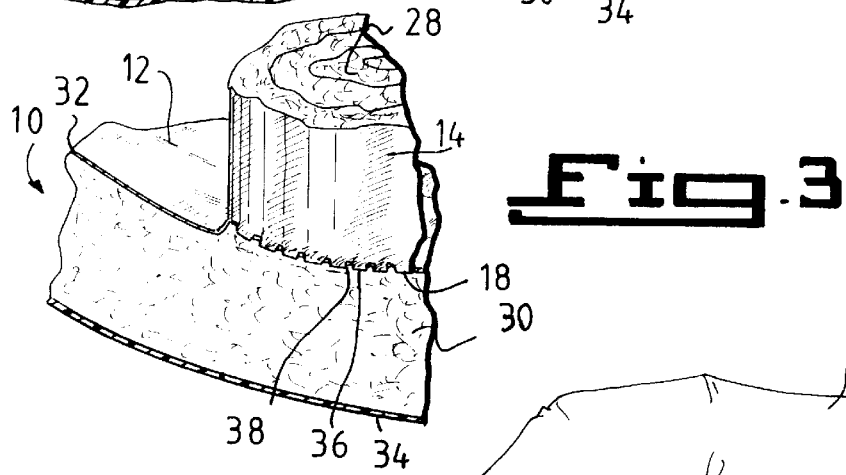
FIG. 3 is an exploded perspective view illustrating the perforated connection of the tampon to the base pad of the combination tampon and menstrual pad of the present invention.

FIG. 3 illustrates an exploded view of the perforated connection 18 between the tampon 14 and the horizontally extending base pad 12. The perforated connection 18 is formed by an alternating pattern of seals 36 and separations 38. The seals 36 connect the tampon 14 to the upper layer 32 of the base pad 12 and the separations 38 are positioned between adjacent seals 36. Thus, each of the separations 38 have an area defined by the tampon 14, the horizontally extending base pad 12 and the seals 36 on either side thereof. The separations 38 form areas of separation between the seals of the tampon 14 and between tampon 14 and horizontally extending base pad 12. The alternating seals 36 and separations 38 form the perforated connection between the tampon 14 and the between tampon and horizontally extending base pad 12.

Figure 4:
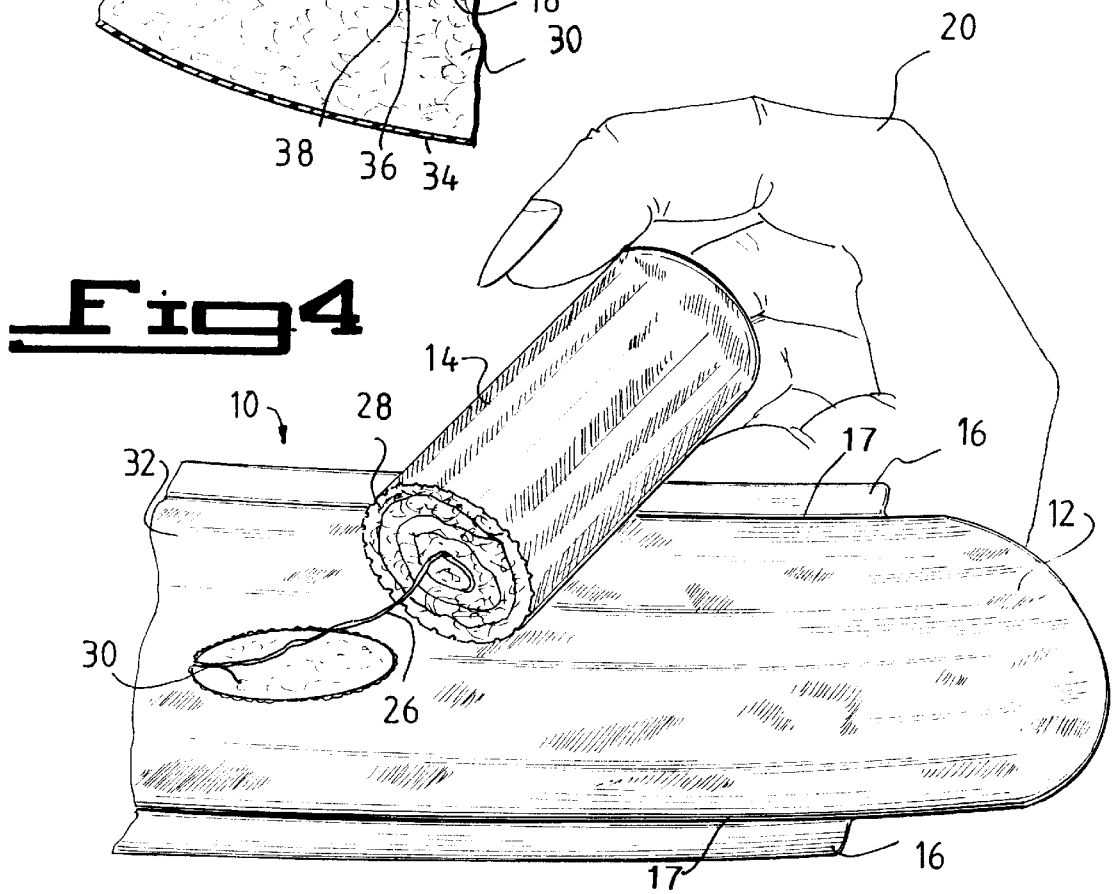
FIG. 4 is a perspective view of the tampon being removed from the base pad of the combination tampon and menstrual pad of the present invention.

When the tampon 14 is grasped by the hand 20 of a user and a twisting force is applied to the tampon 14 along with a pulling force in a direction away from the horizontally extending base pad 12, the seals 36 are caused to break and the tampon 14 becomes disengaged from the base pad 12 as illustrated in FIG. 4. The strand of material 26 is caused to extend between the rolled compressed material 28 forming the tampon 14 and the absorbent material forming the inner layer 30 of the horizontally extending base pad 12 as the tampon 14 is pulled away from the horizontally extending base pad 12. This is because the rolled compressed material 28 forming the tampon 14 and the absorbent material forming the inner layer 30 of the horizontally extending base pad 12 are connected together when the combination tampon and menstrual pad 10 is in its original combined form. Upon separation of the tampon 14 and the horizontally extending base pad 12, the string 26 is broken to thereby fully separate the horizontally extending base pad 12 and the tampon 14 for independent use.

FIG. 5 illustrates the combination tampon and menstrual pad 10 including a gluteal pad 40 extending from the horizontally extending base pad 12. From this view, it can be seen that the gluteal pad 40 includes a fold 42 therein for positioning within the buttocks of a user. The gluteal pad 40 is positioned on one end of the horizontally extending base pad 12 and is of a length substantially equal to the distance from between the legs of the user, up between the buttocks of the user and past the rectum to the top of the cheeks of the user's buttocks, i.e. from the anterior pubis to the tailbone or coccyx. The edges 44 of the gluteal pad 40 taper towards the end of the gluteal pad 40 opposite the connection with the horizontally extending base pad 12 thereby allowing the gluteal pad 40 to easily be positioned between the buttocks of the user. The gluteal pad 40 is of a width greater than that of the base pad 12 as a result of the additional material needed to form the fold 42 for positioning within the buttocks. The gluteal pad 40 acts to absorb any spillage which occurs during secretion of bodily fluids. Spillage of the bodily fluid which are absorbed by the gluteal pad normally occurs due to movement of the user or when the user is lying in a horizontal position. Also illustrated in this figure is an adhesive material 39 positioned on an underside of each of the wings 16. When the wings 16 are folded to wrap around the sides of the undergarment 21, the adhesive material 39 will adhere to the undergarment 21 to hold the combination tampon and menstrual pad 10 in position.

The combination tampon and menstrual pad 10 including a gluteal pad 40 wherein the tampon 14 has been removed is illustrated in FIG. 6. Such combination either includes the perforated connection between the tampon 14 and the horizontally extending base pad 12 or is formed without the tampon 14 connected to the horizontally extending base pad 12. With the tampon 14 removed, the base pad 12 is used in the same manner as a diaper to absorb any bodily fluids secreted by the user.

FIG. 7 illustrates a top perspective view of the combination tampon and menstrual pad 10 including the gluteal pad 40. This view illustrates the flexibility of the combination tampon and gluteal pad 10 for forming to the groin area of the user to thereby provide comfort when used. When used, the fold 42 is caused to extend substantially perpendicular from the gluteal pad 40 so as to fit between the buttocks of the user. The tapering of the sides 44 of the gluteal pad 40 provide for a continuous surface and comfortable fit when used. The extension of the tampon 14 from the base pad 12 is also illustrated in this figure. As can be seen, the angle of extension of the tampon 14 from a horizontal plane changes as the base pad 12 is arced for positioning in the groin area of the user.

The operation of the combination tampon and menstrual pad 10 will now be described with reference to the figures and specifically to FIG. 7. In operation, the user 19 must first decide whether it is desired to use the combination tampon and menstrual pad 10 with or without the tampon 14 extending therefrom. If it is desired to use the combination tampon and menstrual pad 10 without the tampon 14, the user 19 must then grasp the tampon 14 with one hand 20 and turn the tampon 14 while holding the horizontally extending base pad 12 steady, thereby breaking the seals 36 which form the perforated connection 18 between the tampon 14 and the horizontally extending base pad 12. As the user 19 turns the tampon 14, an upwardly directed force should be applied in a direction away from the horizontally extending base pad 12 to remove the tampon 14 therefrom. The string of material 26 extending between the tampon 14 and the horizontally extending base pad 12 is then broken to separate the tampon 14 from the horizontally extending base pad 12 for independent use.

If it is desired to use the combination tampon and menstrual pad 10 with the tampon 14, the covering on the adhesive strip 25 positioned on the underside 23 of the base pad 12 is removed. The tampon 14 is then positioned within either the vaginal opening or another opening as desired and the horizontally extending base pad 12 is positioned beneath the user's undergarment 21 and between the user's legs 48 in the groin area. The adhesive strip 25 will adhere to the undergarment 21 to thereby hold the combination tampon and menstrual pad 10 in position. The wings 16 are positioned to extend from between the user's legs 27 so as to overlap the user's undergarment 21 thereby providing support for holding the horizontally extending base pad 12 in place. The wings 16 are folded about the lateral borders 17 to wrap around the sides of the undergarment 21. The adhesive material 39 on the underside of the wings 16 is now caused to contact and adhere to the undergarment thereby providing added stability against movement. The gluteal pad 40 is now caused to extend from between the user's legs 27 and behind the user 19 for positioning between the user's buttocks whereby the fold 42 extends between the cheeks of the buttocks.

When in this position the tampon 14 is able to absorb most liquid secretions coming from the opening in which it is positioned. Any secretion not absorbed by the tampon 14 may be absorbed by the horizontally extending base pad 12. Any fluids flowing towards the sides of the undergarment may be absorbed by the lateral borders 17 and should any fluid spill over the sides of the undergarment 21 it may be absorbed by the wings 16.

If the user 19 is lying in a horizontal position while secreting a bodily fluid from a body opening in the groin area some of the bodily fluid may spill from between the legs 27 of the user and towards the buttocks. This spillage may be absorbed by the gluteal pad 40. Thus, any bodily fluid secreted from an opening in the groin area of the user 19 can be absorbed by the combination tampon and menstrual pad 10 of the present invention.

From the above description it can be seen that the combination tampon and menstrual pad of the present invention is able to overcome the shortcomings of prior art devices by providing a combination tampon and menstrual pad wherein the tampon is connected to extend from a base pad which is placed beneath a woman's undergarment. The connection between the tampon and base pad may include a perforated connection therebetween allowing the tampon to be removed and used separately from the base pad. The combination tampon and menstrual pad may also include wings extending from the pad for overlapping the sides of the woman's undergarment to provide additional support and a gluteal pad extending from an end of the pad for providing additional absorption of backward spillage occurring when a woman lies in a horizontal position. Furthermore, the combination tampon and menstrual pad of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An absorbent pad for absorbing bodily fluid secreted from a user, said absorbent pad including:
    a) a base pad include first and second length sides and first and second wings, said first and second wings each extending along a respective one of said first and second length sides, and
    b) a cylindrical tampon of fluid absorbing material extending substantially perpendicular to said base pad at a central portion of said base pad said tampon being adapted to be inserted within a body opening of the user when said base pad is positioned outside the body opening and between legs of the user whereby said tampon and absorbent pad absorb body fluids secreted from the body opening, said tampon being removably connected to said base pad by way of a perforated connection along the perimeter of said tampon.

2. The absorbent pad as recited in claim 1, wherein said tampon is formed from a rolled compressed absorbent material.

3. The absorbent pad as recited in claim 1, wherein said base layer includes a first absorbent layer positioned between two fluid permeable layers.

4. The absorbent pad as recited in claim 3, wherein said two fluid permeable layers allow fluid to pass therethrough for absorption by said first absorbent layer.

5. The absorbent pad as recited in claim 1, wherein said base pad includes a first end and said absorbent pad further comprises a gluteal pad extending from a first end of said base pad.

6. The absorbent pad as recited in claim 5, wherein said base pad includes a first end and said absorbent pad further comprises a gluteal pad extending from a first end of said base pad.

7. The absorbent pad as recited in claim 6, wherein said gluteal pad includes first and second tapered sides.

8. The absorbent pad as recited in claim 7, wherein said gluteal pad further comprises a fold extending between said first and second tapered sides for positioning within the user's buttocks during use.

9. The absorbent pad as recited in claim 1, further comprising a first lateral border between said first length side and said first wing and a second lateral border between said second length side and said second wing, said first and second lateral borders providing added absorption of secreted bodily fluids.

10. The absorbent pad as recited in claim 1, further comprising an adhesive strip positioned on a side of said base pad opposite said tampon for securing said base pad to an undergarment of the user.

11. The absorbent pad as recited in claim 10, further comprising an adhesive material positioned on an underside of each of said first and second wings.

12. The absorbent pad as recited in claim 9, further comprising an adhesive material positioned on an underside of each of said first and second wings.

13. The absorbent pad as recited in claim 1, having a string of tampon material joining the material comprising said tampon integrally connecting said tampon to said horizontally extending base pad.

* * * * *